United States Patent [19]

Kümmerer

[11] Patent Number: 4,936,486
[45] Date of Patent: Jun. 26, 1990

[54] DOSING APPARATUS FOR METERING PREDETERMINED QUANTITIES OF A STERILIZING AGENT TO A SPRAY DEVICE

[75] Inventor: Helmut Kümmerer, Nellmersbach, Fed. Rep. of Germany

[73] Assignee: Gasti-Verpackungsmaschinen GMBH, Schwabisch-Hall, Fed. Rep. of Germany

[21] Appl. No.: 361,034

[22] Filed: Jun. 2, 1989

[30] Foreign Application Priority Data

Jun. 7, 1988 [DE] Fed. Rep. of Germany ....... 3819419

[51] Int. Cl.[5] .............................................. B67D 5/22

[52] U.S. Cl. ........................................ 222/42; 222/64; 222/133; 222/145; 222/148; 222/288; 222/318; 222/334; 222/355; 222/356; 222/636; 141/108; 422/33

[58] Field of Search ..................... 222/318, 42, 64, 65, 222/133, 145, 148, 288, 333, 334, 355, 356, 361, 522, 636; 141/108, 110, 358; 422/33

[56] References Cited

U.S. PATENT DOCUMENTS 907,274 12/1908 Neureuther ........................ 222/356

2,167,690 8/1939 Serinis ............................ 222/356 X 3,638,838 2/1972 Marraffino et al. ........... 222/635 X 4,002,268 1/1977 McKinney .

4,474,315 10/1984 Gilbert .......................... 222/356 X

FOREIGN PATENT DOCUMENTS 2128053 12/1972 Fed. Rep. of Germany .

3540161 8/1987 Fed. Rep. of Germany .

8112175 5/1982 France .

*Primary Examiner*—Joseph J. Rolla
*Assistant Examiner*—Gregory L. Huson
*Attorney, Agent, or Firm*—Herbert Dubno

[57] ABSTRACT

The problems of excess flow of a liquid to be dispensed in a metering device, especially for a sterilizing liquid for packings and packaging materials, is solved by pumping the liquid from a supply vessel below the housing of the metering device into the latter and maintaining a bath of the liquid in the latter by overflow back to the supply vessel. A control slider lifts a quantity of the liquid from the bath to an overflow channel from which it flows to a metering chamber and then passes through an upwardly inclined duct to the atomizing and blowing device applying the liquid spray to the packaging materials.

16 Claims, 5 Drawing Sheets

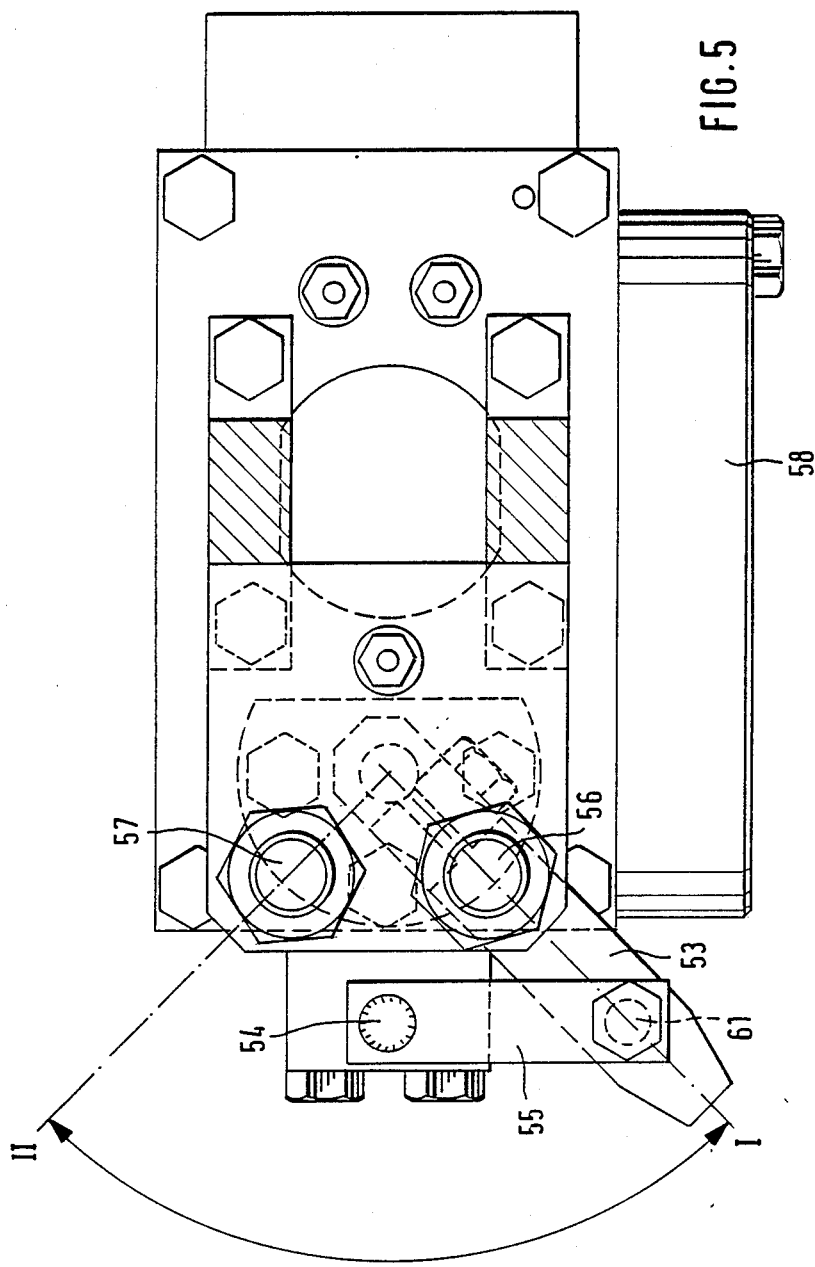

DOSING APPARATUS FOR METERING PREDETERMINED QUANTITIES OF A STERILIZING AGENT TO A SPRAY DEVICE

FIELD OF THE INVENTION

My present invention relates to a device for metering predetermined quantities of liquid as withdrawn from a supply vessel. More particularly, the invention relates to a dosing device, especially for use in the sterilizing of packaging materials, which can supply the metered or dosed medium, generally a liquid substance such as hydrogen peroxide, from a supply vessel via a liquid displacement pump, to an atomizer and spraying device.

BACKGROUND OF THE INVENTION

It is known to make use of a dosing or metering system for metering predetermined quantities of a sterilizing liquid, e.g. hydrogen peroxide, to spray nozzles for atomizing the liquid in entrainment with a carrier gas and directing the liquid onto or into container parts or containers which must be sterilized before they are used to receive the packaged goods, e.g. comestibles.

Such systems are closely associated with packaging machinery and are capable of effecting a noncontaminating sterilization of the packaging just before the packaging is to receive the goods. The packagings may be, for example, cups adapted to receive dairy products and covers or lids which can be applied to the cups.

A dosing device for the purposes described is illustrated, for example, in German Patent No. 35 40 161.

In the system of that patent, the sterilizing agent is atomized and dispersed in a mixture with compressed air, the resulting mixture has turbulence imparted to it and is evaporated by heating as the sterilizing fluid is sprayed on the surfaces of the packaging material or packaging containers to be sterilized by means of the atomizing blower arrangement.

The supply vessel for the sterilizing agent in this system is located above the transport path of the packaging containers or the packaging material.

This has the significant disadvantage under certain operating circumstances that the machine may become functionally unreliable. For example, especially when the machine is brought to standstill and electric current and compressed air supplies to the machine fail, non-sealing nozzles, leaking valves and screw junctions can permit an uncontrolled flow of the sterilizing agent to the atomizing blower device and result in an accumulation and leakage of the sterilizing agent. Not only does an undesirable loss of the sterilizing agent occur, but excessive accumulations of the sterilizing agent in the packaging containers or on the packaging materials may create unsanitary conditions which must be cleaned up at considerable cost and often with losses of the packaging material.

OBJECTS OF THE INVENTION

It is, therefore, the principal object of the present invention to provide a dosing device for the purposes described which will allow an absolutely reliable and exact dosing of the sterilization agent and will prevent undesirable overdosing as may occur with conventional systems.

Another object of the invention is to provide an improved apparatus for feeding the atomizing nozzle arrangement which will avoid the drawbacks of the earlier system described.

Another object is to provide an efficient, reliable, accurate and simple apparatus for dosing liquid substances like hydrogen peroxide and other liquid sterilizing agents.

SUMMARY OF THE INVENTION

These objects and others which will become more apparent hereinafter are attained, in accordance with the present invention, in an apparatus which comprises:

a supply vessel containing a quantity of the liquid substance;

an atomizing spray device disposed above the supply vessel and receiving metered quantities of the liquid substance for dispersing the liquid substance in a carrier fluid and directing the carrier fluid and the liquid substance dispersed therein against the article;

a metering device connected between the supply vessel and the spray device for supplying the metered quantities of the liquid substance to the spray device, the metering device comprising:

a metering housing located above the vessel and adapted to receive a liquid bath of the substance, the housing being formed with an inlet for delivering the liquid substance to the bath and an outlet from which excess liquid can overflow from the bath, a control slider displaceable in the housing between a lower position wherein a portion of the slider is immersed in the bath and an upper position wherein the portion of the slider is withdrawn from the bath, the portion being formed with a pocket receiving a quantity of the liquid substance, a runoff channel formed in the housing and communicating with the pocket in the upper position of the control slider for discharging the quantity of the liquid substance received in the pocket from the control slider a dosing chamber on the housing positioned to receive the quantity of the liquid substance discharged from the pocket through the channel in free flow therefrom, and a duct connecting the dosing chamber with the atomizing spray device; and means for feeding the liquid substance from the vessel to the inlet.

The apparatus of the invention is preferably used for the metering of predetermined quantities of a sterilizing liquid for sterilizing packaging materials and containers in which the difference in heights of the supply vessel and the dosing chamber and between the latter and the atomizing blower device completely excludes an afterfeed or overdosing of the latter with the liquid.

This assurance against afterflow is ensured by the mechanical setup of the apparatus and particularly the height difference between the liquid level of the bath and the dosing chamber and the difference between the height level of the latter and the atomizing blower device or devices.

The apparatus is so arranged that it can be used in all machines in which hydrogen peroxide sterilization is possible and can be used to upgrade machines handling the packaging materials. An important advantage is that there is no need to provide a large quantity of hydrogen peroxide at any particular height, for example, above the height of the eyes of machine service personnel, thereby obtaining an additional safety factor. In a preferred embodiment of the invention, the control slide is shiftable in a guide bush which extends downwardly into the liquid bath and is formed at its low end with an opening communicating with the bath. In the lower position of the control slide, a passage in the latter, communicating with the pocket, can register with this opening in the guide bush or sleeve.

In addition, the housing can have its inlet opening into the bath at the bottom thereof while the overflow outlet for the bath lies above the inlet. In this manner the sterilizing agent can flow into the bath and into the control slide when the latter is in its lower position, so that this portion of the control slide is continuously filled with the sterilizing agent. It is advantageous for the control slide to be hollow and its recess or pocket fashioned in a ladel-shape.

The cooperation of the metering or dosing chamber with the dosing cylinder and the control slide is simplified when the dosing chamber is provided as an upwardly open measuring container whose bottom is connected by an outlet with a somewhat upwardly extending duct running to the atomizing and blowing device or devices.

The periphery of the guide bush can be formed by a ring which forms a part of the runoff channel delivering the liquid to the measuring chamber.

This ensures an effective bridging of the space between the control slider on the one hand and the metering chamber on the other.

It has been found to be especially advantageous to make the dosing chamber as a replaceable part, i.e. to provide a plurality of mutually substitutable dosing chambers dimensioned for different quantities and which can be selectively brought into the metering position and held there.

Replacement of a dosing chamber can be effected simply by providing a plurality of chambers on a control slider which is rotatable in the housing preferably about an axis parallel to the axis of the control slide. An actuating mechanism can be provided for the swingable slider and can include a ram carrying the slider and biased by a spring in the direction of the sealing surface of the housing against which the slider rides and against which the outlet of the dosing chamber can seal.

The upper or free end of the ram carries an actuating lever whose angular position can be read by a proximity sensor. The various liquid levels in the device can be detected by respective liquid level sensors, especially in the region of the liquid bath and the upper positioned metering chamber. Control of the apparatus can be effected by a programmed controller using microprocessor technology and data storage.

Apparatus of the type described in accordance with the invention can be provided separately for the cup sterilization and lid sterilization. Alternatively, the apparatus can include means for operating two metering devices having a common supply vessel.

BRIEF DESCRIPTION OF THE DRAWING

The above and other objects, features and advantages of my invention will become more readily apparent from the following description, reference being made to the accompanying highly diagrammatic drawing in which:

FIG. 5 is a section taken along the line V—V of FIG. 4.

SPECIFIC DESCRIPTION

Figure 1:
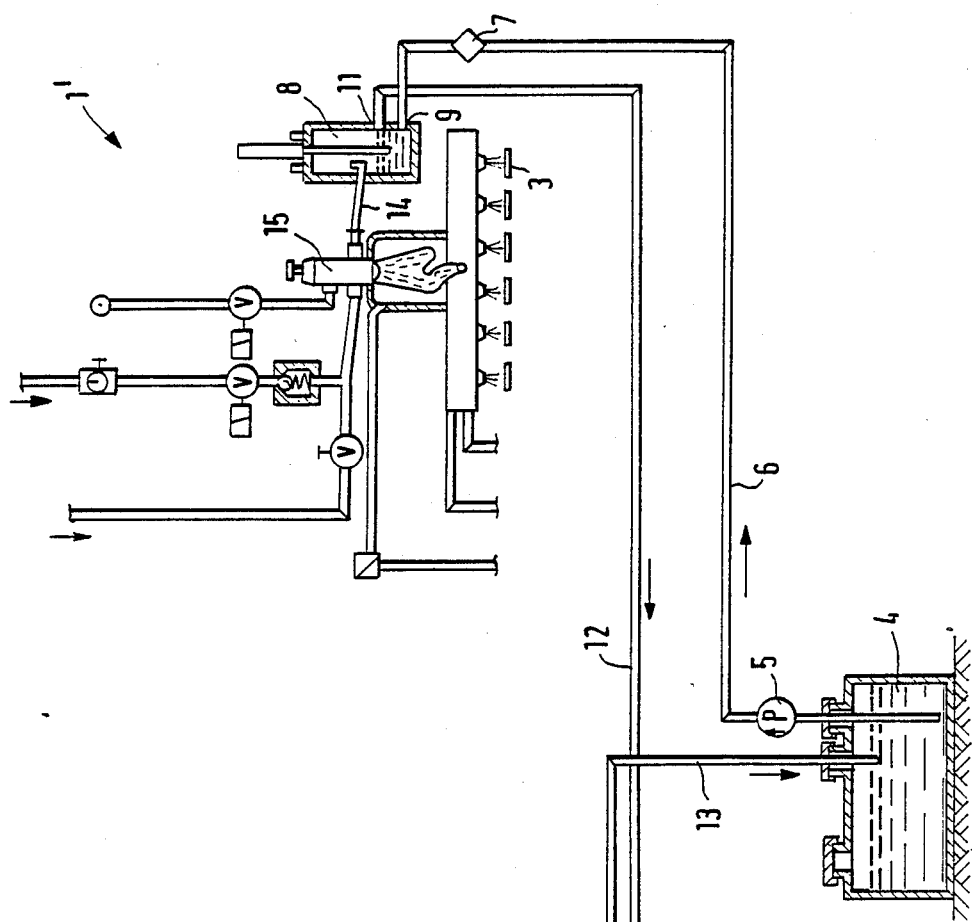
FIG. 1 is a flow diagram representing a sterilization apparatus for cup and lid sterilization having respective hydrogen peroxide metering devices.
Figure 1:
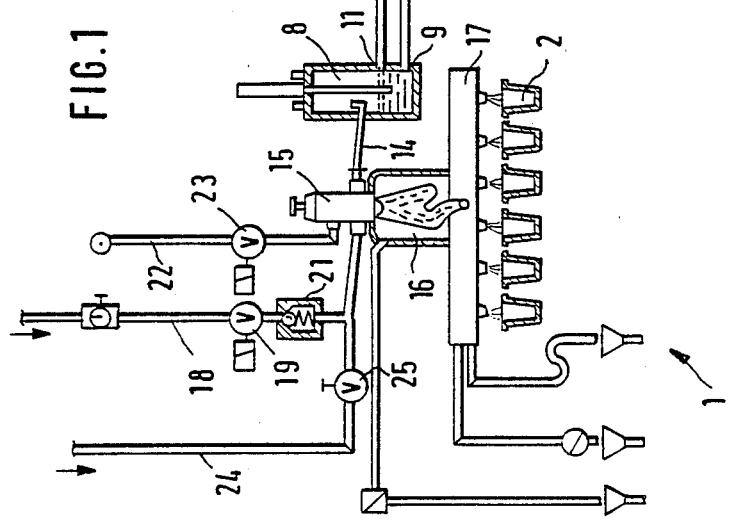

FIG. 1 shows at 1 a station for the sterilization of packaging containers 2 and at 1' a station for the sterilization of flat covers or lids 3 for these packaging containers. The apparatus may be provided in a conventional packaging machine.

The devices at stations 1 and 1' are largely identical so that the description below of the apparatus for container sterilization will be understood to be applicable as well to an apparatus for lid sterilization.

For the two sterilization apparatuses, a common supply vessel 4 is provided and contains the liquid sterilization medium, for example hydrogen peroxide. The supply vessel is connected via a liquid displacement pump 5 with a feed line 6 and a filter 7 with the upper 1 of the two metering devices 8 of the respective apparatuses. Details of the metering devices 8 will be developed in the description of the container sterilization apparatuses. The overflow from the upper metering device 8 is communicated via a pipe 12 to the inlet 9 of the lower metering device 8, i.e. the metering device associated with the container sterilization apparatus and overflow sterilization liquid is returned to the vessel 4.

A metering device 8 illustrated only schematically in FIG. 1 but in greater detail in FIGS. 2–5, comprises in addition to the inlet bore 9, an overflow bore 11 located above the inlet bore 9. In FIG. 1, the pipe 12 connects the overflow bore 11 of the upper metering device 8 with the inlet bore 11 of the upper metering device 8 with the inlet bore of the lower metering device. In the lower metering device, the inlet bore, has also been shown at 9 while the overflow bore is represented at 11 and is connected by the pipe 13 with the storage vessel 4.

Each measuring device 8 has an upwardly inclined duct 14 running to a two-component nozzle 15 and an evaporation chamber 16 of an atomizing blowing device 17.

The device 17 is provided with an array of dispensing nozzles for directing the dispersed sterilization medium, e.g. hydrogen peroxide, into the containers or onto the lids 3.

To the two-component nozzle 15, a first pipe 18 with a control 19 and a check valve 21 are connected as well as a second control pipe 22 with a control valve 23.

Through the pipe 18 clean atomizing air at a controllable pressure of 0 to 2.5 bar can be fed.

Control air with a pressure, for example, of 5 bar can be fed through the pipe 22.

A third pipe 24 with a control valve 25 is also connected to the nozzle 15 to supply the water for nozzle and system cleaning as may be required.

The aforedescribed control valves are provided in an identical manner for the lid sterilization apparatus 1' and have the same functions as have been described so that further description is unnecessary.

The measuring device 8 is described in greater detail in connection with FIG. 2. The metering device comprises a housing 26 formed at its bottom with the inlet 9 and above the inlet 9 with the overflow outlet 11.

The housing 26 is closed at its upper end by a cover 27 in which a guide bush 28 for receiving a control slider 29 is mounted.

The control slider 29 is hollow and is provided close to its lower end with a ladel-shaped pocket or recess while, at its upper end, it is connected by a coupling plate 32 with a piston and cylinder unit 33 by means of which the control slider 29 is displaceable between an upper position and a lower position.

An inlet port 34 communicating with the pocket 31 is provided in a side wall of the control slider 29 and registers in the lower position of the slider 29, with a throughgoing opening in the bush 28 disposed generally at the level of the overflow housing 11.

Located somewhat above this opening 35 is a ring 36 mounted on the bush 28 and forming part of a runoff channel 37 which is inclined downwardly and to the left, the remainder of the channel being formed in the wall of the bush 28.

Somewhat below and laterally offset from the outlet end of the channel 37, there is positioned a dosing cylinder 38 which is formed with a metering chamber forming a measuring container 39.

The chamber 39 is upwardly open and is connected via an overflow edge 41 with a bath 42 of the liquid to be dispensed, lying below this overflow edge.

The liquid level in the bath 42 is limited by the overflow formed by the bore 11 of the housing 26.

In the bottom of the metering chamber 39, an outlet port 43 is provided which communicates with the upwardly inclined duct 14 extending to the atomizing and blower device lying somewhat thereabove.

The runoff channel 37 can be aligned with the pocket in the control slider 29 when the latter is raised to discharge the sterilizing liquid raised to the level of the mouth of the runoff channel.

The levels of the sterilizing liquid can be monitored in the region of the liquid bath 42 in the housing 26 and in the metering chamber by level sensors 44, 45 and 46.

The metering cylinder can be fixed in the housing 26. In this case, of course, the metering device has only a fixed dosing volume. When a variety of dosing volumes must be supplied to the atomizer blower device, the dosing cylinder or measuring container can be formed as a replaceable part. In this case, differently dimensioned dosing cylinders can be selectively inserted into the liquid metering position and locked in place.

Figure 3:
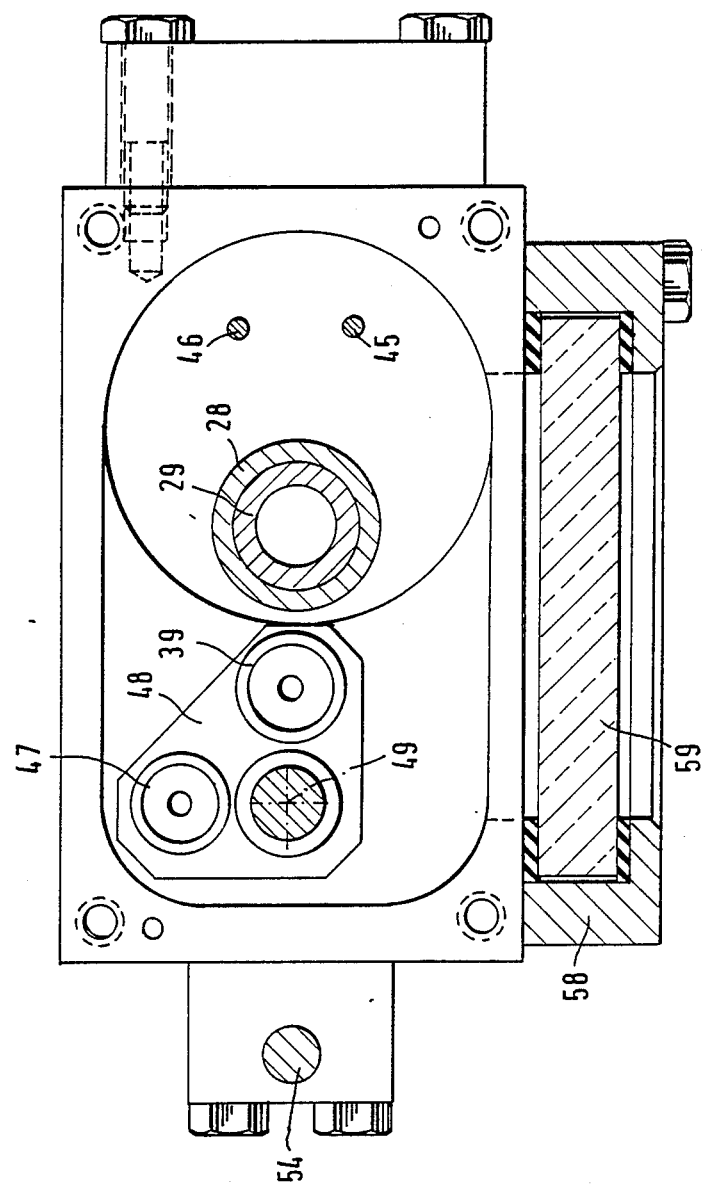
FIG. 3 is a section along the line III—III of FIG. 2.
Figure 4:
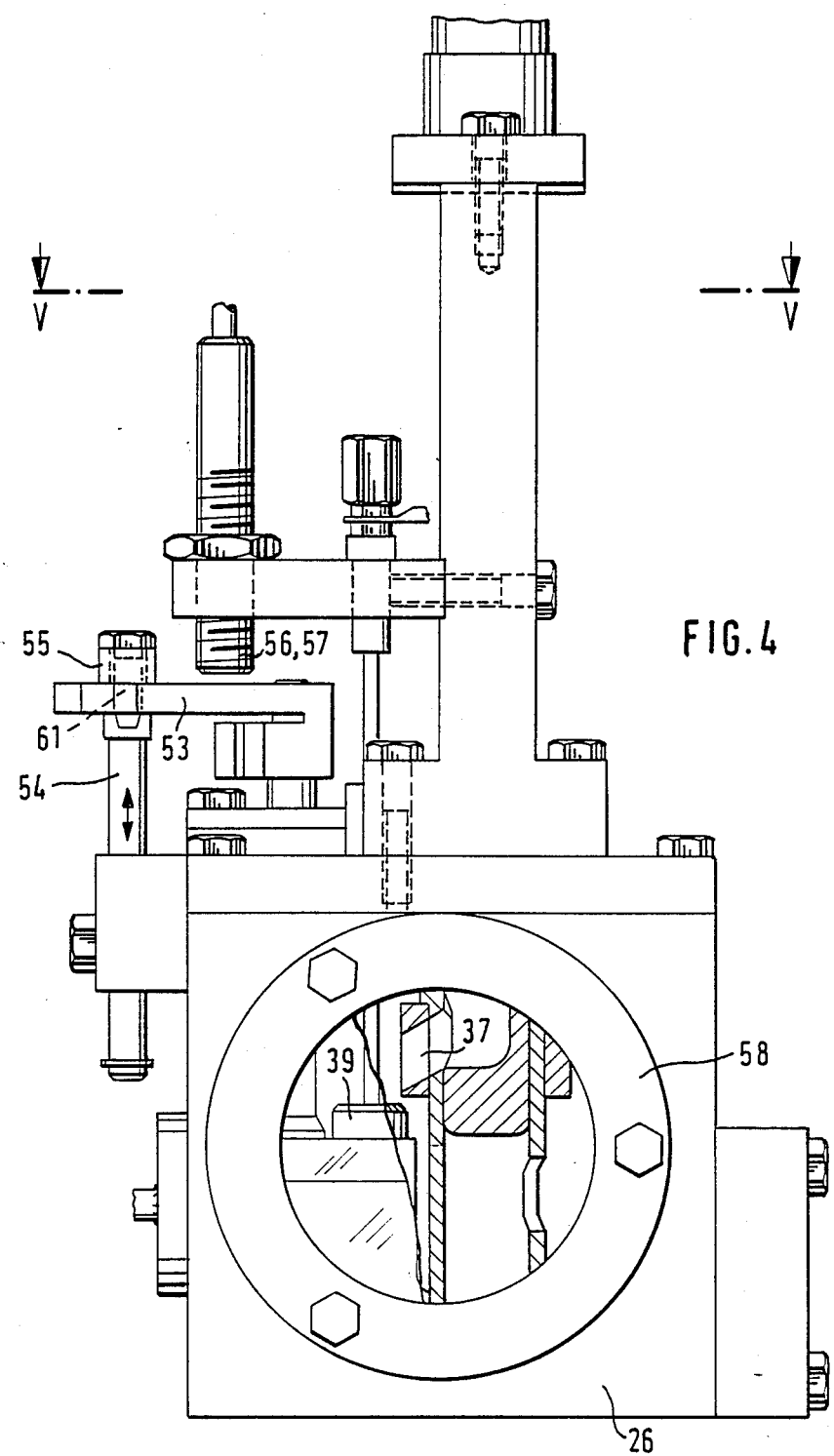
FIG. 4 is a front elevational view of the metering device.

A system which allows two such cylinders to be used for metering different quantities of liquid has been illustrated in greater detail in FIGS. 3-5.

Apart from the normal metering cylinder 39, a further metering cylinder 47 is provided. The two metering cylinders 37 and 47 are connected on a common slider 38 which is swingable about an axis 49 parallel to the longitudinal axis of the control slider 29 through 90°.

In this manner, either metering cylinder 39 or metering cylinder 47 can be located in the liquid metering position.

To displace the slider 48, I provide an actuating mechanism which comprises a ram 52 connected to member 48 and biased downwardly by a spring 51 to maintain the sealing action against the surface which has a hole registering with the outlet in the measuring cylinder at the opposite end of the ram from the pivotable slide 48, the ram is provided with an actuating lever 53 (FIGS. 4 and 5).

The actuating lever 53 can be locked in place in two angular positions I and II by, for example, a locking finger or stud 61 on the lever 55 carried by a vertical movable pin 54 guided in the housing. The finger 61 can drop into the hole in the actuating lever 53 to retain it against movement. When the finger 61 is lifted out of this hole, however, the lever must be swung in one sense or the other. The respective positions of the actuating lever 53 can be detected and signalled by proximity signals 56 and 57.

Figure 2:
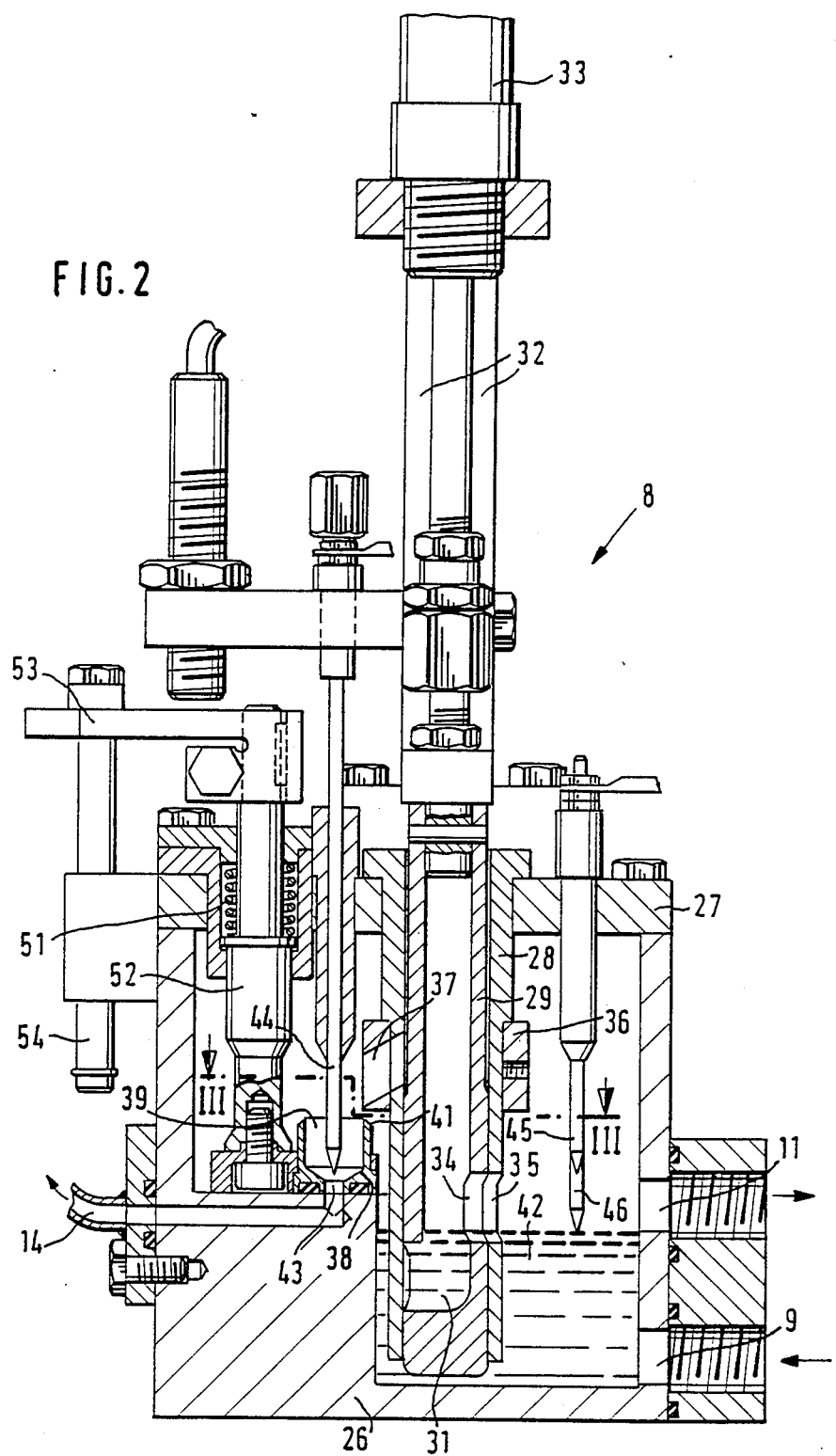
FIG. 2 is a cross-sectional view showing the metering device drawn to an enlarged scale.

In FIG. 2, the control slider 29 is shown in its lower position in which its pocket collects the liquid to be dispensed. In FIG. 4 the control slider 29 is shown in its upper position in which it is dispensing or has dispensed the liquid through the runoff channel 37 into the metering chamber 39. In this position, at least observation of the control slider can be ensured by providing on the side of the housing 26 a mounting 28 with a viewing glass. The metering device of the invention operates as follows: with a continuous driving of the displacement pump 5, sterilizing liquid is forced via a pipe 6 and filter 7 into the inlet 9 of the uppermost sterilizing apparatus so that the hydrogen peroxide bath of the metering device 8 thereof is maintained. The liquid overflows into the lower inlet 9 of the lower metering device 8 to form the hydrogen peroxide bath therein.

In the lower position of the respective control slider 29 illustrated in FIG. 2, the scoop-shaped pocket 31 fills with the liquid sterilizing agent.

When the control slider is then raised into its upper position with the aid of the piston and cylinder unit 33, e.g. into the position shown in FIG. 2 the sterilizing agent flows from the pocket 31 via the runoff channel 37 into the metering chamber 39 of the dosing cylinder 38. The volume of the chamber 39 is smaller than the contents of the pocket 31 so that excess sterilizing liquid flows over the edge 41 back into the bath 42 in the housing 26. A precisely measured volume of the liquid is thus contained in the chamber 39 and is delivered by duct 14 to the atomizing blower device so that a precise quantity of the sterilizing agent can be directed into the packings or onto the lids 3.

I claim:

1. An apparatus for dosed application of a liquid substance to an article, especially for the application of a sterilizing agent such as hydrogen peroxide to packages, comprising:

a supply vessel containing a quantity of said liquid substance;

an atomizing spray device disposed above said supply vessel and receiving metered quantities of said liquid substance for dispersing said liquid substance in a carrier fluid and directing said carrier fluid and the liquid substance dispersed therein against said article;

a metering device connected between said supply vessel and said spray device for supplying said metered quantities of said liquid substance to said spray device, said metering device comprising:

a metering housing located above said vessel and adapted to receive a liquid bath of said substance, said housing being formed with an inlet for delivering said liquid substance to said bath and an outlet from which excess liquid can overflow from said bath, a control slider displaceable in said housing between a lower position wherein a portion of said slider is immersed in said bath and an upper position wherein said portion of said slider is withdrawn from said bath, said portion being formed with a pocket receiving a quantity of said liquid substance, a runoff channel formed in said housing and communicating with said pocket in said upper position of said control slider for discharging the quantity of said liquid substance received in said pocket from said control slider, a dosing chamber on said housing positioned to receive the quantity of said liquid substance discharged from said pocket through said channel in free flow therefrom, and a duct connecting said dosing chamber with said atomizing spray device; and means for feeding said liquid substance from said vessel to said inlet.

2. The apparatus defined in claim 1 wherein said chamber is an upwardly open measuring container formed with a bottom having an outlet communicating with said duct and said duct is upwardly inclined from said outlet at said bottom of said measuring container to said atomizing spray device.

3. The apparatus defined in claim 1 wherein said chamber is replaceable mounted in said housing to enable control of measured quantities of said liquid substance by selection of the chamber size.

4. The apparatus defined in claim 1, further comprising liquid-level sensors responsive to the level of said bath and to a level of liquid in said chamber.

5. The apparatus defined in claim 1 wherein said housing is formed with a guide bush extending downwardly into said bath and having an opening in a side wall located at least in part below a level of said bath, said slider being guided in said bush between said positions and having a port registering with said opening in said lower position and also communicating with said pocket, said inlet opening into said bath at a bottom portion of said housing, said outlet opening into said bath at a location above said inlet.

6. The apparatus defined in claim 5 wherein said slider is hollow and said pocket is ladle-shaped.

7. The apparatus defined in claim 5 wherein said bush is formed on an outer periphery with a ring formed with at least part of said runoff channel.

8. The apparatus defined in claim 1 wherein said measuring chamber is one of a plurality of measuring chambers provided in said housing, said metering device further comprising means for selectively positioning said chambers in a liquid-metering position and for locking a selected one of said chambers in said liquid-metering position.

9. The apparatus defined in claim 8 wherein said measuring chambers are mounted on a swingable slide pivotal about an axis substantially parallel to a longitudinal axis of said control slider for angular displacement of said swingable slide to selectively position said chambers at said liquid-metering position.

10. The apparatus defined in claim 9, further comprising an actuating mechanism connected to said swingable slide for pivotally displacing same.

11. The apparatus defined in claim 10 wherein said mechanism comprises a ram connected to said swingable slide and mounted in said housing to rotate about the pivot axis of said swingable slide, a spring braced against said ram and pressing said ram downwardly, and an actuating lever connected to an upper end of said ram for displacing same, said apparatus further comprising a proximity sensor juxtaposed with said lever for signalling an angular position of said lever.

12. The apparatus defined in claim 11 wherein said mechanism further comprises a guide pin displaceable on said housing substantially parallel to said axes, an arresting lever on said guide pin, and a locking pin on said arresting lever engageable in a bore formed in said actuating lever to releasable retain said actuating lever in one angular position thereof.

13. The apparatus defined in claim 12 wherein said housing is formed with a guide bush extending downwardly into said bath and having an opening in a side wall located at least in part below a level of said bath, said slider being guided in said bush between said positions and having a port registering with said opening in said lower position and also communicating with said pocket, said inlet opening into said bath at a bottom portion of said housing, said outlet opening into said bath at a location above said inlet.

14. The apparatus defined in claim 13 wherein said slider is hollow and said pocket is ladle-shaped.

15. The apparatus defined in claim 14 wherein said chamber at said liquid-metering position is an upwardly open measuring container formed with a bottom having an outlet communicating with said duct and said duct is upwardly inclined from said outlet at said bottom of said measuring container to said atomizing spray device.

16. The apparatus defined in claim 15 wherein said bush is formed on an outer periphery with a ring formed with at least part of said runoff channel.

* * * * *